(12) United States Patent
Leong et al.

(10) Patent No.: US 10,092,773 B2
(45) Date of Patent: Oct. 9, 2018

(54) SUBJECT TARGET TISSUE SPECIFIC TEMPLATE DEVICE

(71) Applicant: Analogic Corporation, Peabody, MA (US)

(72) Inventors: David Leong, Seabrook, NH (US); John P. O'Connor, Andover, MA (US)

(73) Assignee: Analogic Corporation, Peabody, MA (US)

( * ) Notice: Subject to any disclaimer, the term of this patent is extended or adjusted under 35 U.S.C. 154(b) by 80 days.

(21) Appl. No.: 15/124,217

(22) PCT Filed: Mar. 7, 2014

(86) PCT No.: PCT/IB2014/059541
§ 371 (c)(1),
(2) Date: Sep. 7, 2016

(87) PCT Pub. No.: WO2015/132636
PCT Pub. Date: Sep. 11, 2015

(65) Prior Publication Data
US 2017/0014641 A1    Jan. 19, 2017

(51) Int. Cl.
*A61N 5/00* (2006.01)
*A61N 5/10* (2006.01)
(52) U.S. Cl.
CPC .......... *A61N 5/1007* (2013.01); *A61N 5/103* (2013.01); *A61N 5/1027* (2013.01); *A61N 2005/1012* (2013.01)
(58) Field of Classification Search
CPC ..................... A61N 5/1007; A61N 2005/1012

USPC .......................................... 600/1-8
See application file for complete search history.

(56) References Cited

U.S. PATENT DOCUMENTS

| 7,527,593 B2 * | 5/2009 | Fidel | A61B 8/12 600/1 |
|---|---|---|---|
| 2011/0009748 A1 | 1/2011 | Greene et al. | |
| 2012/0302890 A1 | 11/2012 | Strong | |

OTHER PUBLICATIONS

International Search Report for PCT/IB2014/059541 published as WO2015/132636 dated Sep. 11, 2015.
Roy, JN, et al., CT-Based Optimized Planning for Transperineal Prostate Implant with Customized Template, I. J. Radiation Oncology vol. 21, No. 2, Jul. 1991.

(Continued)

*Primary Examiner* — John Lacyk
(74) *Attorney, Agent, or Firm* — Anthony M. Del Zoppo, III; Daugherty & Del Zoppo Co., LPA

(57) ABSTRACT

A subject target tissue specific template device (300) that includes a block of material (302) and a plurality of apertures (310) in the material. An aperture of the plurality of apertures is located in the block of material at a location that corresponds to an area of interest identified in an image of an anatomical region of interest of a subject and transferred to an image of block of material with no aperture, which is geometrically aligned with the image of the anatomical region of interest of the subject. A method includes aligning, with a computing system, an image of anatomical tissue of interest with an image of a grid, marking at least one area of interest of tissue of interest within the image of tissue of interest, transferring the marking to the image of the grid, and saving the image of a grid with the marking as a file in an electronic format.

20 Claims, 6 Drawing Sheets

(56) References Cited

OTHER PUBLICATIONS

Pompeu-Robinson, A, Immobilization and catheter guidance for breast brachytherapy, Int. J CARS (2012) 7:65-72.
Bentel, et al., Transperineal Templates for Brachytherapy Treatment of Pelvic Malignancies—A Comparison of Standard and Customized Templates, Int. J. Radiation Oncology Biol. Phys. vol. 19, pp. 751-758 (Mar. 1990).
Baumert, et al., A Novel Technique Using Customised Templates for the Application of Fractioned Interstitial HDR Brachytherapy to the Tumour Bed in Soft-tissue Sarcomas Located in the Extremities, Clinical Oncology (2004) 16:457-460.
Disposable Grid Template from Civco Medical Solutions, http://www.civco.com/mmi/ultrasound/positioning/brachytherapy/disposable-template-grids-PID5150.htm—date retrieved Sep. 2, 2016.
Hayes, J., Three size brachytherapy templates. Can be found at http://libertymedicalinc.com/—date retrieved Sep. 2, 2016.
IZI Medical Brachytherapy template—http://izimed.com/—can be found at http://www.hellotrade.com/izi-medical-products/prostate-brachytherapy-template-grids.html—date retrieved Sep. 2, 2016.
Disposable Prostate Template from Kobold—can be found at https://www.elekta.com/brachytherapy/kobold-applicators.html—date retrieved Sep. 2, 2016.
Brachytherapy Grids—can be found at http://cpmedical.com/wp-content/uploads/2012/07/Brachy-Grids-product-matrix-06-2012.pdf—date retrieved Sep. 2, 2016.

\* cited by examiner

SUBJECT TARGET TISSUE SPECIFIC TEMPLATE DEVICE

RELATED APPLICATION

This application is a national filing of PCT application Serial No. PCT/IB2014/059541, filed Mar. 7, 2014, published as WO2015/132636 on Sep. 11, 2015. This application claims priority to PCT application Serial No. PCT/IB2014/059541, published as WO2015/132636 on Sep. 11, 2015.

TECHNICAL FIELD

The following generally relates to a subject target tissue specific template device and is described with particular application to a template grid for brachytherapy; however, the subject target tissue specific template device is also amenable to other procedures such as cryotherapy, focal therapy, whole organ treatment, and biopsy, and/or other procedures.

BACKGROUND

In brachytherapy, clinicians have utilized a physical grid having a standard pattern of apertures to guide needle insertion in connection with the placement of radioactive seeds within an anatomical organ of interest such as the prostate. Such a grid is also used for biopsies and other procedures. An example of such a grid is shown in FIG. 1. In FIG. 1, a square grid 102 includes a two-dimensional array of apertures 104, including first size apertures 106 and second size apertures 108, within a material 110. The apertures 104 are preformed and arranged equidistant from each other, center-to-center.

The illustrated grid 102 includes first graphical indicia (i.e., alphabetical characters, in this example) along the columns 114 and second graphical indicia (i.e., numbers, in this example) along the rows 116. The graphical indicia 114 and 116 provides a frame of reference, or a reference coordinate system (x,y) for each of the apertures 104. For example, the aperture $104_1$ corresponds to coordinates B,3. The procedure plan is created based on this coordinate system. The procedure plan, in general, indicates which apertures 104 will be used during the procedure, referencing the apertures 104 by their coordinates.

In FIG. 1, a closed line 118, which identifies a sub-region of grid 102 used for a particular procedure plan, is superimposed over the grid 102. The line 118 represents an outer perimeter 118 of the anatomical organ of interest. The outer perimeter 118 is determined, for example, by imaging a volume of the patient that includes the anatomical organ of interest, e.g., via CT or MR. The anatomical organ of interest is segmented from the volume. This may include drawing the line 118 via software drawings package. The segmented anatomical organ of interest is aligned with an image representing the grid 108. The outer perimeter 118 marking is transferred to the image representing the grid 102.

FIG. 2 (FIG. 3 in U.S. 2011/0009748 A1) shows use of such a grid in a procedure. Note that 104, 202 and 204 are not part of the original FIG. 3 in U.S. 2011/0009748 A1, but have been added to FIG. 2 for explanatory purposes.

In FIG. 2, an ultrasound probe 130 is supported by a housing 128, and a grid 115 is supported by a connecting arm 126 to the housing 128. The grid 115 is similar to that of 102 in FIG. 1 in that it includes a standard pattern of apertures 104. The ultrasound probe 130 is shown partially inserted into the rectum 3 of the patient. A clinician 200, based on coordinates for an aperture 104 from the procedure plan, inserts a needle 50 through the aperture 104 and guides the needle 50 to the anatomical organ of interest 2, using an ultrasound image generated with data acquired by the ultrasound probe 130 to guide the needle 50 to an area of interest within the anatomical organ of interest 2.

Unfortunately, the areas of interest are limited by the standard pattern of the apertures 104 of the grid 115 to only the areas reachable through the apertures 104. For example, in FIG. 2, areas 202 are reachable through the apertures 104. However, where there is no aperture between the two shown apertures 104, an area 204 between the areas 202 is not reachable by the needle 50. As such, areas of interest to a clinician may not be reachable when using the grid 115 and, thus, the areas accessible utilizing the grid 115 for a particular procedure may not be the areas of interest to the clinician. Furthermore, the clinician may have to keep a mental note of which apertures have already been used so as not to use the same aperture twice and repeat an already completed step of the plan.

SUMMARY

Aspects of the application address the above matters, and others.

In one aspect, a subject target tissue specific template device that includes a block of material and a plurality of apertures in the material. An aperture of the plurality of apertures is located in the block of material at a location that corresponds to an area of interest identified in an image of an anatomical region of interest of a subject and transferred to an image of block of material with no aperture, which is geometrically aligned with the image of the anatomical region of interest of the subject.

In another aspect, a method includes aligning, with a computing system, an image of anatomical tissue of interest with an image of a grid, marking at least one area of interest of tissue of interest within the image of tissue of interest, transferring the marking to the image of the grid, and saving the image of a grid with the marking as a file in an electronic format.

In another aspect, a method includes receiving, by a computer, a signal from a physical subject specific grid indicating an instrument entered an aperture of multiple apertures of the physical subject specific grid. The multiple apertures correspond to positions defined in a procedure plan prior to creating the subject target tissue specific template device. The method further includes indicating the aperture through a message generating by the computer.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

Figure 1:
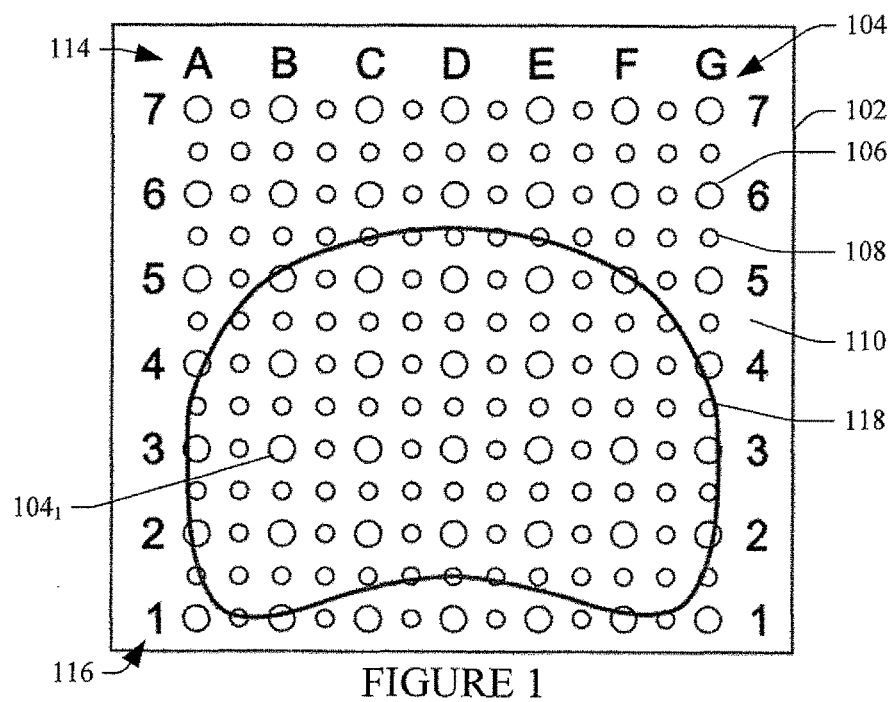
FIG. 1 illustrates an example prior art template grid, including a standard two dimensional array of apertures.
Figure 2:
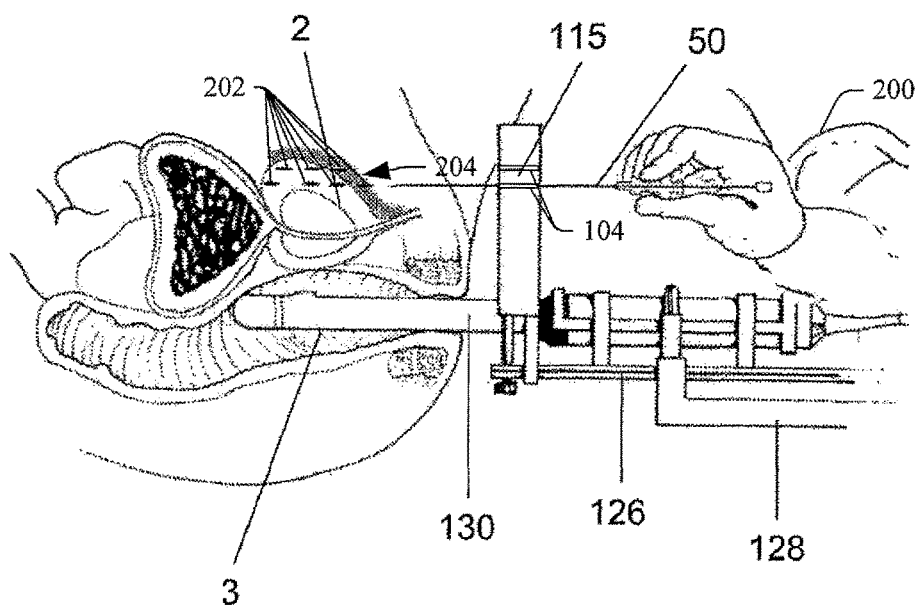
FIG. 2 illustrates example use of the prior art template grid in a brachytherapy procedure.
Figure 3:
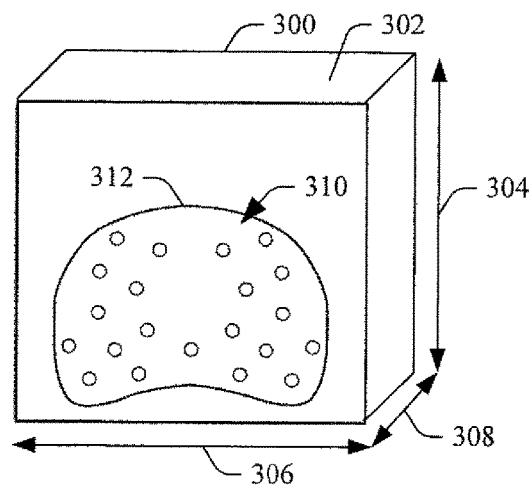
FIG. 3 schematically illustrates an example of a subject target tissue specific template device.

FIG. 3 schematically illustrates an example subject target tissue specific template device 300.

The illustrated subject target tissue specific template device 300 is rectangular in shape. Other shapes, such as square, elliptical, circular, and/or other shapes are contemplated herein. The subject target tissue specific template device 300 may be washable or disposable, and includes a block of material 302 such as aluminum, a polymer (e.g., a thermoplastic polymer such as polycarbonate), and/or other material.

The subject target tissue specific template device 300 has a height ("H") 304, a width ("W") 306 and a depth ("D") 308. An example of a suitable height 304 is between three (3) to eighty (80) millimeters (mm). An example of a suitable width 306 is between three (3) to eighty (80) mm. An example of a suitable depth 308 is between one (1) to ten (10) mm. Other heights, widths, and/or depths are contemplated herein.

The subject target tissue specific template device 300 further includes a plurality of material free regions or apertures 310, which extend completely through the block of material 302. The apertures 310 are located within a sub-region 312, which corresponds in geometry to a geometry of the anatomical tissue of interest. The spacing and/or sizes of the apertures 310 are based on the patient and the procedure, and are either semi or fully customized for a patient, for procedures such a brachytherapy, cryotherapy, focal therapy, whole organ treatment, customized biopsy sampling, and/or other procedure.

Each aperture 310 has a diameter that allows passage of a needle having a gauge in a range from 14 to 20 GA, or other over or non-overlapping range. For instance, an aperture 310 may have a diameter that allows a 17 GA (1.473 mm) and/or an 18 GA (1.270 mm) needle to pass through, unobstructed. For this, the diameter may be in a range of just larger than the largest needle gauge to about 0.100 mm larger than the largest needle gauge or higher. Generally, the spacing and diameters of the apertures 310 allow a clinician to guide near organ boundaries and/or to place a tip of the needle near or at tissue of interest. An aperture 310 can be straight or curved and be tubular (as shown) or include one or more flat internal walls.

As described in greater detail below, each of the apertures 310 can be individually (or group-wise) positioned within the sub-region 312 based on the subject. As such, the spacing between one pair of apertures 310 may be the same or different than the spacing between another pair of apertures 310. In one instance, the subject target tissue specific template device 300, having apertures 310 that are positioned as such, mitigates restricting access to areas of interest by the clinician, which may allow for access to optimal areas of the anatomical tissue of interest. Furthermore, by having patient specific apertures 310, a procedure may have less apertures, relative to a configuration in which the apertures 310 are arranged in a standard pattern, and areas of interest by the clinician are not accessible.

Figure 4:
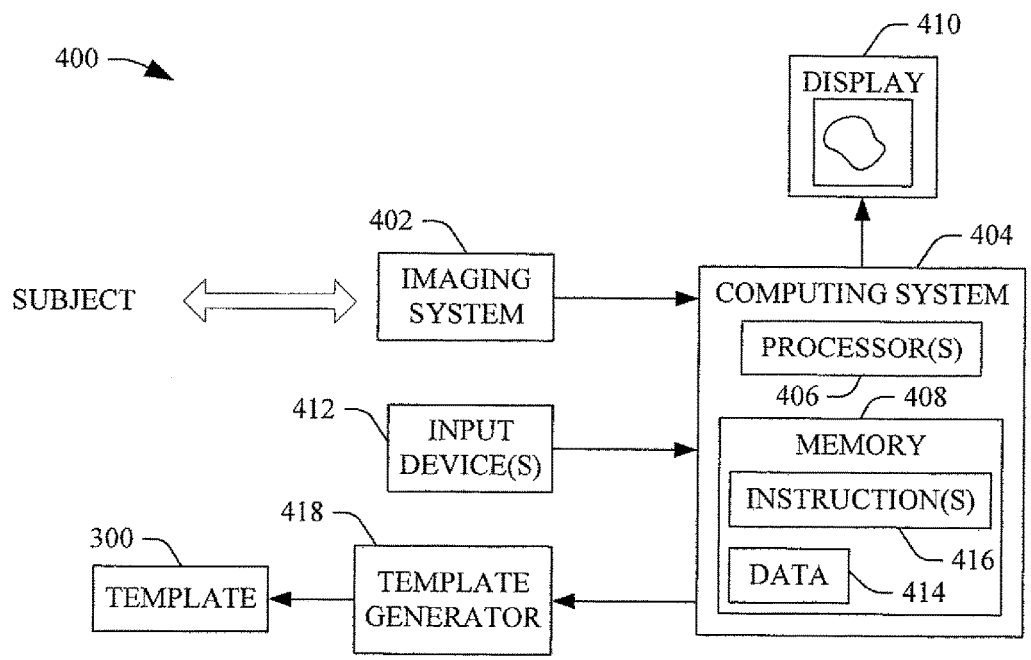
FIG. 4 schematically illustrates an example system that determines subject specific aperture locations for the subject target tissue specific template device.

FIG. 4 schematically illustrates an example system 400 for creating the subject target tissue specific template device 300.

The system 400 includes an imaging system 402, which can be an ultrasound, computed tomography, magnetic resonance, x-ray, and/or other imaging system. The imaging system 402 scans the subject, and, in particular, a region of the subject including the anatomical tissue of interest. The imaging system 402 outputs the raw data and/or images reconstructed therefrom.

A computing system 404 includes a processor 406 (e.g., a central processing unit or CPU, a microprocessor, etc.) and computer readable storage medium ("memory") 408, which excludes transitory medium, but includes physical memory and/or other non-transitory memory. The computing system 404 further includes an output device(s) such as a display 410, and an input device(s) 412 such as a mouse, keyboard, a touch sensitive region of a touchscreen, etc.

The computing system 404 receives the data output by the imaging system 402. Alternatively, the computing system 404 receives the data from a data repository such as a database, a server, or the like. The data can be stored in the memory 408. The memory 408 can also store other data 414 and computer readable instructions 416. The computer readable instructions 416, when executed by the processor 406, runs software that allows a user to segment anatomical tissue of interest from the data. The software program may include an auto-segmenting tool and/or tools for manual segmentation.

The computer readable instructions 416, when executed by the processor 406, further runs software that spatially aligns the segmented image with an image of a template device that does not include any of the apertures 310. The computer readable instructions 416, when executed by the processor 406, further runs software for planning a procedure. This may include receiving an input from the input device 412 that indicates one or more areas of interest in the segmented data.

The one or more areas of interest, depending on the procedure, may correspond to radioactive seed locations for a brachytherapy procedure, biopsy locations for a biopsy procedure, target areas for cryotherapy, etc. The one or more areas of interest can be identified and marked using the display 410, which, in the illustrated embodiment, displays a sagittal plane of the segmented anatomical tissue of interest. Axial and/or coronal planes can alternatively or additionally be displayed and used to identify and mark one or more areas of interest.

The computer readable instructions 416, when executed by the processor 406, further runs software that transfer the one or more areas of interest marked on the image onto the image of the template spatially aligned with the image. Note that the image of the template is spatially aligned with the image and segmented data so that the image of the template represents a "virtual" physical template in that it is aligned with the segmented data in a manner in which the physical template will align with the actual anatomical tissue of interest.

The processor 406 stores, in electronic format (e.g., a "file"), the image of the template with the one or more areas of interest in the memory 408 and/or conveys, wire and/or wirelessly (e.g., over a network), the image of the template with the one or more areas of interest to another device. Additionally or alternatively, the image of the template with the one or more areas of interest can be conveyed to the other device through portable storage medium (e.g., CD, DVD, optical disk, memory stick, smartphone, etc.) and/or otherwise, such as "cloud" based and/or other storage.

A template generator 418 receives the image of template with the one or more areas of interest. The template generator 418, based on the received image template with the one or more areas of interest, generates a physical template, which will be specific to the patient and based on the procedure plan for the patient. The template generator 418 may include a three-dimensional (3D) printer, which is configured to make a 3D solid object from a digital model, which, in this instance, is the received image of the template. The subject target tissue specific template device 300 can alternatively be generated through machining, extrusion, molding, and/or other process.

At least one of a location, a size, a spacing between, a number, etc. corresponding to the apertures 310 is specific to the subject and varies between subjects. Again, the resulting subject target tissue specific template device 300 includes apertures 310 that are positioned to access areas of interest of the anatomical tissue of interest identified by the clinician, rather than limit the clinician to a predetermined pattern of apertures, which are not specific to any subject. That is, the procedure plan determines the apertures 310, rather than the aperture 310 dictating the procedure plan.

Figure 5:
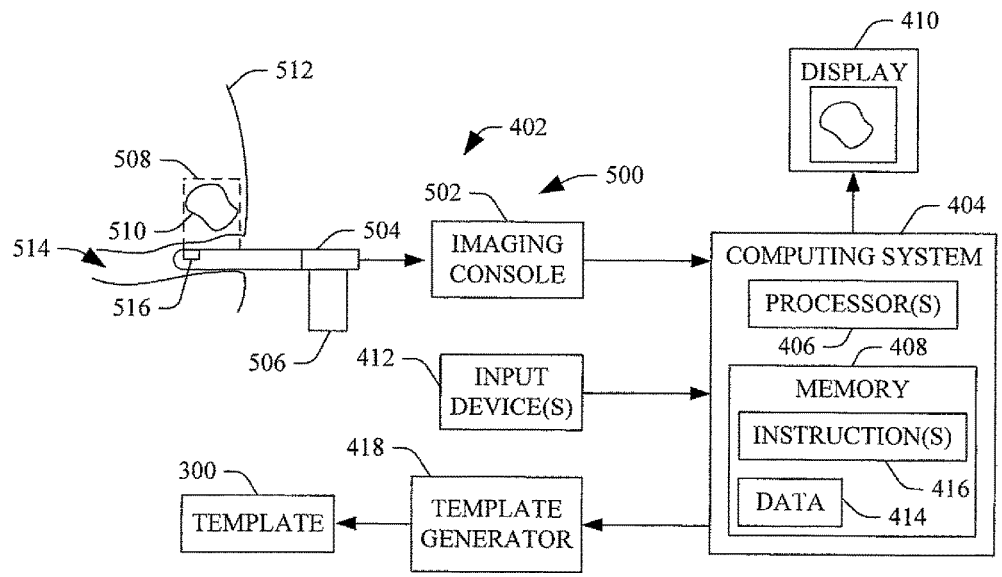
FIG. 5 schematically illustrates another example system that determines subject specific aperture locations for the subject target tissue specific template device.

FIG. 5 shows a variation of FIG. 4 where the imaging system 402 is an ultrasound imaging system 500, with a console 502 and a probe 504, which houses a transducer array 516. The probe 504 is supported by a physical support 506. In this example, the ultrasound imaging system 500 is used to scan a field of view (FOV) 508 which include a prostate 510 of a subject 512.

For this, the ultrasound probe 504 is partially inserted into the rectum 514 of the patient. The transducer array 516, in one instance, can acquire a 3D volume of the FOV 508 and hence the prostate 510. In another instance, the transducer array 516 acquires 2D transverse slices or sagittal slices, which, in aggregation, cover the entire FOV 508 and hence the prostate 510. For the latter, the ultrasound probe 504 may be translated, rotated and/or otherwise maneuvered to acquire such slices.

Figure 6:
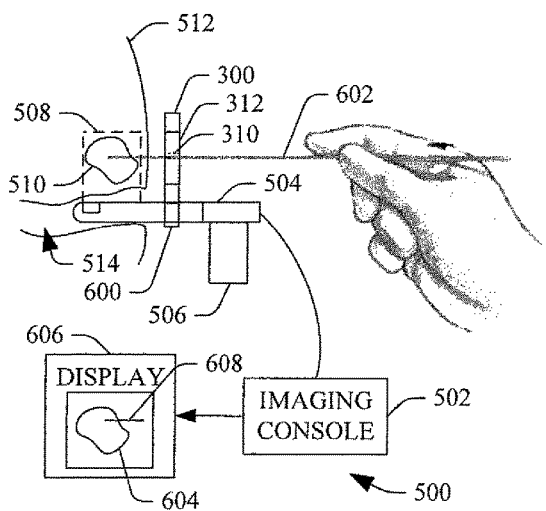
FIG. 6 schematically illustrates the subject target tissue specific template device affixed to an ultrasound probe.

FIG. 6 schematically illustrates the subject target tissue specific template device 300 in use. In this example, the subject target tissue specific template device 300 is affixed to the probe 504 through an element 600. The element 600 can be a clamp, a bracket, and/or other support that may be removabley attached to the probe 504 and/or the subject target tissue specific template device 300 or fixedly attached to at least one of the probe 504 and/or the subject target tissue specific template device 300. In a variation, the subject target tissue specific template device 300 is not attached to the ultrasound probe 504. In this variation, the ultrasound probe 504 is tracked independently to the subject target tissue specific template device 300.

FIG. 6 also shows an instrument 602, which is a needle, that has been passed through one of the apertures 310 and to the prostate 510 via an image 604 displayed through a display 606. A portion 608 of the instrument 602 in the FOV 508 is also shown in the displayed image 604. The displayed portion 608 of the instrument 602 can be used by the clinician to identify when the instrument 602 is at an area of interest in the anatomical tissue of interest.

For a brachytherapy procedure, the clinician can plant one or more seeds when at the area of interest, for a biopsy procedure, the clinician can trigger the biopsy when at the area of interest, etc. In the illustrated embodiment, the displayed image 604 is a sagittal plane through the anatomical tissue of interest. The clinician can move the probe 504 so that the displayed sagittal plane corresponds to the plane of the instrument 602. In a variation, the procedure plan is provided to a robot, which implements the procedure.

Figure 7:
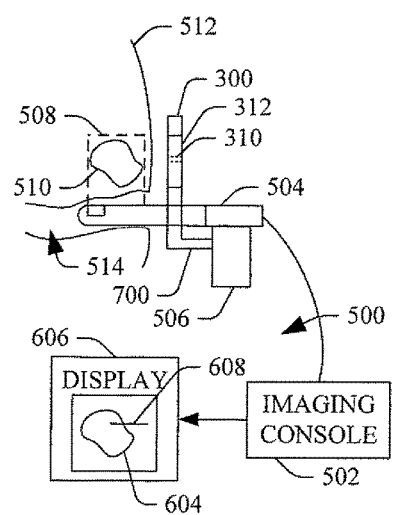
FIG. 7 schematically illustrates the subject target tissue specific template device affixed to a support supporting the ultrasound probe.

FIG. 7 shows a variation of FIG. 6 in which the subject target tissue specific template device 300 is affixed to the physical support 506 through a physical structural support member 700.

FIGS. 8, 9, 10 and 11 show a variation in which the subject target tissue specific template device 300 includes a sensing device(s) 800 within an aperture(s) 310.

Figure 8:
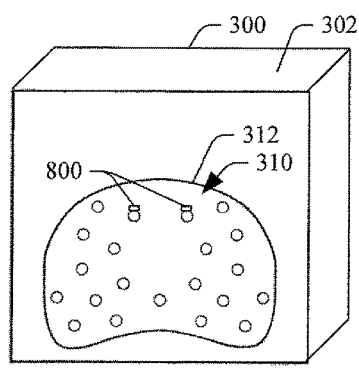
FIG. 8 schematically illustrates a variation of the subject target tissue specific template device, which includes aperture sensors.

FIG. 8 only shows two sensing devices 800 in connection with two apertures 310. However, it is to be understood that the subject target tissue specific template device 300 can include more or less sensing devices 800. It is also to be understood that an aperture 310 can include more than one sensing device 800 and/or a sensing device 800 can be used with more than one aperture 310.

The sensing device 800 of an aperture 310, in response to sensing the instrument 602 (FIG. 6) in the corresponding aperture 310, emits or transmits a signal, which indicates the instrument 602 entered the corresponding aperture. The signal identifies the particular aperture 310. The sensing device 800 may include a capacitive sensor, a magnetic sensor, a coil, and/or other sensor.

The sensing device 800, in one instance, measures a change in capacitance as the instrument 602 enters and/or passes through the aperture 310. In another instance, the sensing device 800 senses a change in a magnetic field applied to the aperture 310. In yet another instance, the sensing device 800 generates an electrical current and/or voltage in response to the instrument 602 entering and/or passing through the aperture 310.

Figure 9:
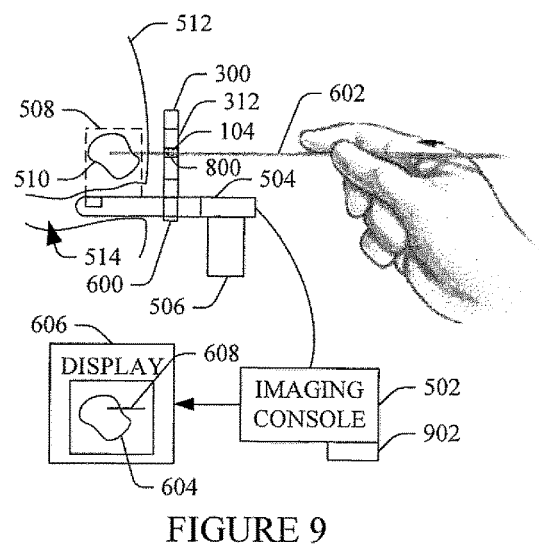
FIG. 9 schematically illustrates a variation of FIG. 6 that includes the subject target tissue specific template device of FIG. 9.

FIG. 9 shows the subject target tissue specific template device 300 of FIG. 8 with the configuration of FIG. 6. In this embodiment, the signal from a sensing device 800 is conveyed to an interface 902 of the imaging console 502 through a cable and/or wireless technology (e.g., RF, IF, optical, etc.).

Figure 10:
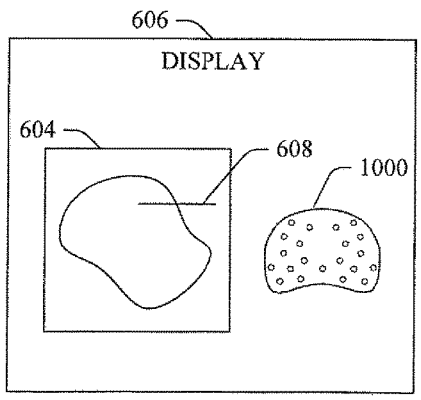
FIG. 10 illustrates an example display indicating which apertures have been used.

FIG. 10 shows an example display which provides a visual indication as to which apertures have been used. In FIG. 10, a "virtual" template device representation 1000, which mimics the sub-region 312 of the subject target tissue specific template device 300, is displayed alongside the display of the image 604 of a plane of the anatomical tissue of interest. In this embodiment, the imaging console 502, in response to receiving the signal from the sensing device 800 (FIG. 9), superimposes indicia over the representation 1000.

For example, where the needle 602 is inserted through an aperture 310 and the corresponding sensing device 800 convey the signal, the console 502, in response to the signal, places an "X" of the corresponding aperture in the representation 1000. In another example, the console 502 highlights the corresponding aperture in the representation 1000 using color and/or gray scale. In another example, the console 502 removes the aperture and/or highlighting from the representation 1000. In yet another example, the console 502 highlights the aperture to use for the next insertion.

Figure 11:
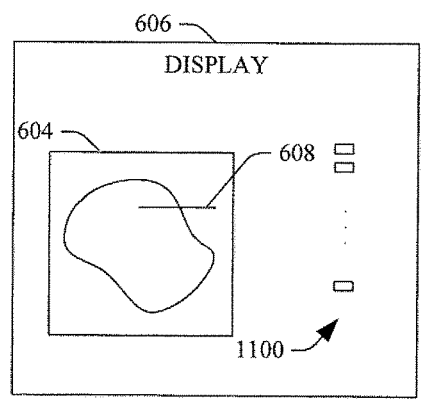
FIG. 11 illustrates another example display indicating which apertures have been used.

FIG. 11 shows a variation in which the visual indication includes a list of aperture coordinates 1100. This list, in one instance, includes the coordinates of each aperture 310 of the subject target tissue specific template device 300 to be used in the procedure. Likewise, highlighting can be added to and/or removed from the list 1100, an aperture 310 can be removed from the list, etc. to indicate an aperture 310 has been used.

In general, the sensing device 800 allows identification of which apertures 310 have been used and/or are to be used. In one instance, this mitigates the clinician reusing an already used aperture 310 and/or using a wrong aperture 310. The signal from the sensing device 800 can also be stored in memory, and referred to in a subsequent procedure, and/or used to alert the clinician (via a visual and/or audible device) that an incorrect and/or already used aperture 310 is being used.

Figure 12:
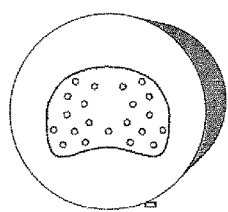
FIG. 12 schematically illustrates a variation of the subject target tissue specific template device, which is cylindrical in shape.
Figure 13:
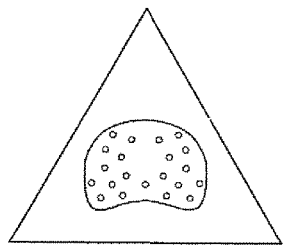
FIG. 13 schematically illustrates a variation of the subject target tissue specific template device, which is triangular in shape.
Figure 14:
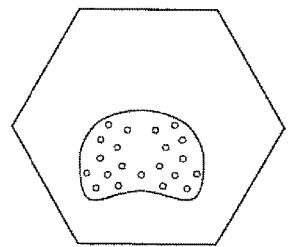
FIG. 14 schematically illustrates a variation of the subject target tissue specific template device, which is hexagonal in shape.

FIGS. 12, 13 and 14 show other configurations of the subject target tissue specific template device 300. In FIG. 12, the subject target tissue specific template device 300 is circular in shape. In FIG. 13, subject target tissue specific template device 300 is triangular in shape. In FIG. 14, the subject target tissue specific template device 300 is hexagonal in shape. Other geometries are also contemplated herein.

Figure 15:
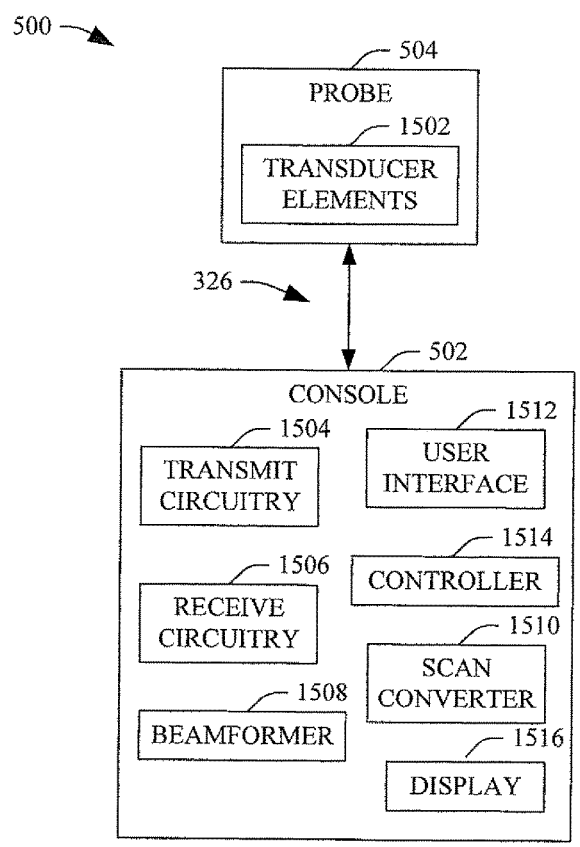
FIG. 15 schematically illustrates an example ultrasound imaging system that can be used in connection with the embodiments described herein.

FIG. 15 illustrates an example of the ultrasound imaging system 500 in FIGS. 5-7 and 9.

The ultrasound probe 504 includes a transducer array with a plurality of transducer elements 1502. The transducer array can be linear, curved, and/or otherwise shaped, fully populated, sparse and/or a combination thereof, etc. The transducer elements 1502 can be operated in 2D, 3D and/or 4D mode. The transducer elements 1502 transmit ultrasound signals and receive echo signals.

The console 502 includes transmit circuitry 1504 that selectively actuates or excites one or more of the transducer elements 1502. More particularly, the transmit circuitry 1504 generates a set of pulses (or a pulsed signal) that are conveyed to the transducer elements 1502. The set of pulses actuates a set of the transducer elements 1502, causing the transducer elements 1502 to transmit ultrasound signals into an examination or scan field of view.

The console 502 further includes receive circuitry 1506 that receives a set of echoes (or echo signals) generated in response to the transmitted ultrasound signals. The echoes, generally, are a result of the interaction between the emitted ultrasound signals and the object (e.g., flowing blood cells, organ cells, etc.) in the scan field of view. The receive circuitry 1506 may be configured for spatial compounding, filtering (e.g., FIR and/or IIR), and/or other echo processing.

A beamformer 1508 processes the received echoes. In B-mode, this includes applying time delays and weights to the echoes and summing the delayed and weighted echoes.

A scan converter 1510 scan converts the data for display, e.g., by converting the beamformed data to the coordinate system of a display or display region used to visually present the resulting data.

A user interface (UI) 1512 include one or more input devices (e.g., a button, a knob, a slider, etc., touchscreen and/or physical mechanical device) and/or one or more output devices (e.g., a liquid crystal display, a light emitting diode, etc.), which allows for interaction with the system 500.

A controller 1514 controls the various components of the system 500.

A display 1516 visually displays the US imaging data. The display 1516 can be part of the console 502 and/or separate therefrom.

Figure 16:
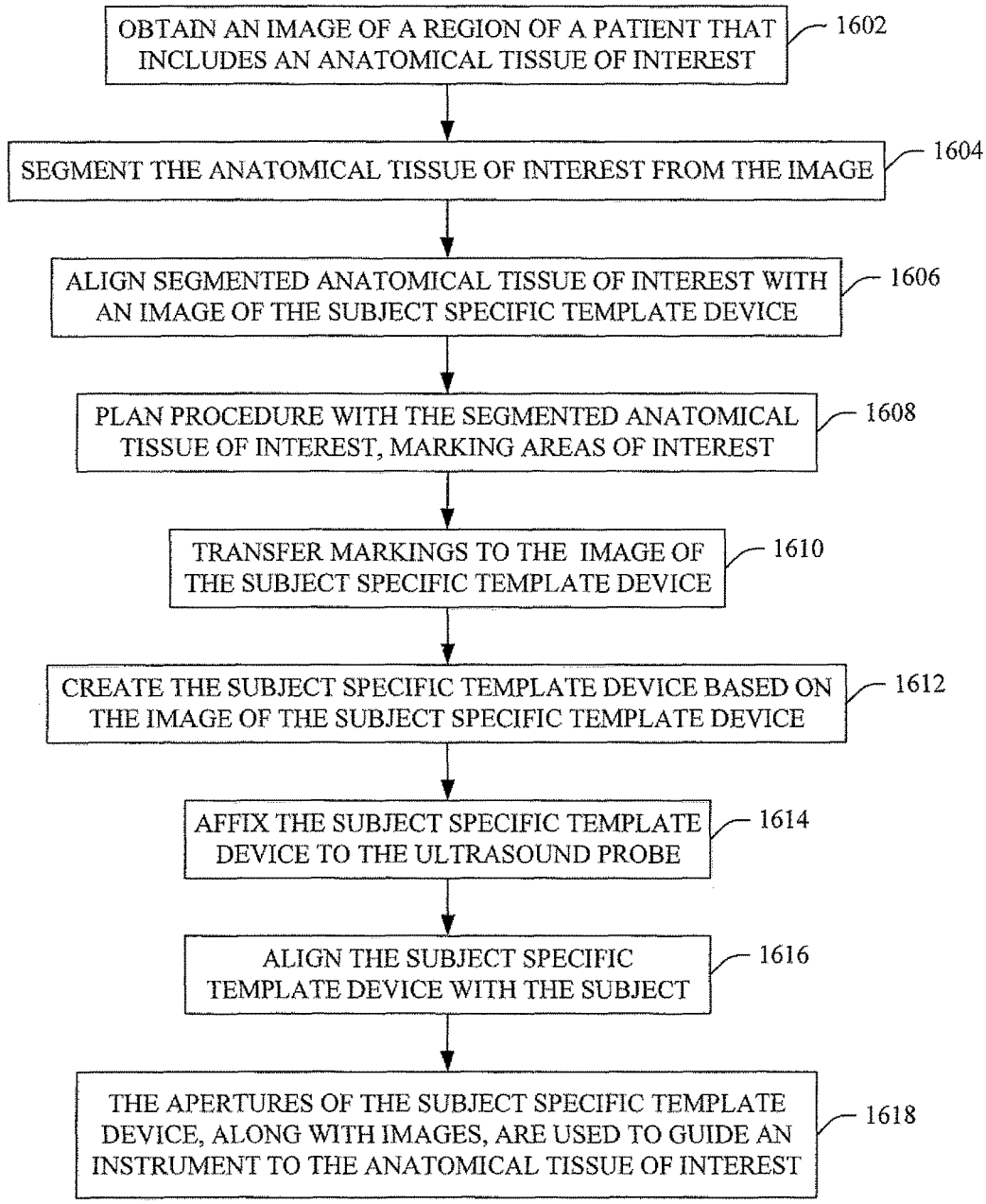
FIG. 16 schematically illustrates an example method in accordance with the description herein.

FIG. 16 illustrates an example method.

It is to be understood that the following acts are provided for explanatory purposes and are not limiting. As such, one or more of the acts may be omitted, one or more acts may be added, one or more acts may occur in a different order (including simultaneously with another act), etc.

At 1602, an image of a region of a patient that includes an anatomical tissue of interest is obtained. This may include scanning the subject and/or retrieving an image from a data repository.

At 1604, the anatomical tissue of interest is segmented from the image. This may include using manual, semi-automatic, and/or automatic software based segmentation tools.

At 1606, the segmented image is aligned with an image of the subject specific template device. This may include using manual, semi-automatic, and/or automatic software based registration and/or alignment tools.

At 1608, a procedure (e.g., brachytherapy, cryotherapy, focal therapy, whole organ treatment, biopsy, etc.) is planned, based on the segmented image, by marking one or more areas of interest on the segmented image.

At 1610, the markings are transferred to the image of the subject specific template device. This may include using manual, semi-automatic, and/or automatic software based tools.

At 1612, of the subject target tissue specific template device 300 is created based on the image of the subject specific template device with the markings.

At 1614, of the subject target tissue specific template device 300 affixed to an ultrasound probe or, alternatively, a support.

At 1616, of the subject target tissue specific template device 300 is aligned with the subject for the procedure.

At 1618, the apertures 310 of the subject target tissue specific template device 300, along with the images, are used to guide an instrument to the anatomical tissue of interest of the subject.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A subject target tissue specific template device, comprising:

a block of material; and a plurality of apertures in the block of material,
wherein the plurality of apertures is located in the block of material at a location that corresponds to an area of interest identified in an image of an anatomical region of interest of a subject previously geometrically aligned with the block of the material without the plurality of apertures; and
at least one sensing device located within at least one of the plurality of apertures, wherein the at least one sensing device includes a capacitive sensor and is configured to sense an entrance of an instrument into the at least one aperture and, in response thereto, generate a signal indicative of the at least one aperture, which identifies the at least one aperture.

2. The subject target tissue specific template device of claim 1, wherein the subject specific template device has a depth between one to ten millimeters.

3. The subject target tissue specific template device of claim 1, wherein the aperture has a diameter, wherein the diameter has a dimension that passes a predetermined gauge instrument.

4. The subject target tissue specific template device of claim 1, wherein the subject specific template device has a height and a width, and the height is between three and one hundred millimeters and the width is between three and one hundred millimeters.

5. The subject target tissue specific template device of claim 1, further comprising:
an element configured to affix to an ultrasound probe or a support supporting the ultrasound probe.

6. The subject target tissue specific template device of claim 1, wherein the at least one sensing device includes a magnetic sensor configured to sense a change in a magnetic field applied to the aperture.

7. The subject target tissue specific template device of claim 1, wherein the at least one sensing device includes a coil configured to generate an electrical current and/or voltage in response to the instrument entering and/or passing through the aperture.

8. The subject target tissue specific template device of claim 1, wherein the plurality of apertures are located in only a sub-region of the material.

9. The subject target tissue specific template device of 1, wherein the plurality of apertures are not arranged in the material based on a pre-determined pattern of equally spaced apertures.

10. The subject target tissue specific template device of claim 1, wherein a number and a location of the plurality of apertures is semi or fully customized to the object.

11. A method, comprising:
aligning, with a computing system, an image of tissue of interest with an image of a grid;
marking at least one area of interest of tissue of interest within the image of tissue of interest;
transferring the marking to the image of the grid;
saving the image of a grid with the marking as a file in an electronic format;
modifying, based on the file, a physical grid that does not include any material free regions to include at least one material free region corresponding to the marking of the image of a subject specific grid, creating a physical object specific grid; and
installing at least one capacitive sensing device within the at least one material free region.

12. The method of claim 11, wherein the subject specific template device has a depth between one to ten millimeters.

13. The method of claim 12, wherein the subject specific template device has a height between three to eighty millimeters.

14. The method of claim 11, further comprising:
employing a 3D printer to create, based on file, the physical subject specific grid and the at least one material free region.

15. The method of claim 11, further comprising:
arranging the at least one material free regions in the grid based on a predetermined procedure plan, which is created prior to creating the physical subject specific grid.

16. The method of claim 11, wherein the material free region has a diameter, which receives a predetermined gauge instrument.

17. The method of claim 11, further comprising:
detecting an instrument entered the material free region with the capacitive sensor of the physical subject specific grid;
generating a signal indicative thereof; and
displaying visual indicia that indicate the instrument entered the material free region based on the signal.

18. The method of claim 17, further comprising:
storing the signal; and
referencing the signal in a subsequent procedure.

19. The method of claim 11, further comprising:
detecting an instrument entered the material free region with the capacitive sensor of the physical subject specific grid; and
providing a notification in response to previously detecting the instrument entered the material free region.

20. The method of claim 12, wherein the subject specific template device has a width between three to eighty millimeters.

* * * * *